United States Patent [19]

Sekiguchi et al.

[11] Patent Number: 5,152,900

[45] Date of Patent: Oct. 6, 1992

[54] METHOD FOR PREPARING PACKAGED STERILIZED MINERAL WATER, METHOD FOR PRODUCING STERILIZED CONTAINER FOR PACKAGING THE SAME AND PACKAGED STERILIZED MINERAL WATER

[75] Inventors: Kazuya Sekiguchi, Ikoma; Masao Taguchi, Osaka; Masayuki Nakatani, Nara; Tomoyuki Seki, Suita; Takaaki Shimizu; Mahito Orii, both of Nara, all of Japan

[73] Assignee: House Food Industrial Co., Ltd., Osaka, Japan

[21] Appl. No.: 651,941

[22] Filed: Feb. 7, 1991

[30] Foreign Application Priority Data

| Feb. 7, 1990 | [JP] | Japan | 2-27856 |
| Feb. 7, 1990 | [JP] | Japan | 2-27857 |
| Feb. 7, 1990 | [JP] | Japan | 2-27858 |
| Feb. 26, 1990 | [JP] | Japan | 2-45072 |

[51] Int. Cl.$^5$ .................................. B01D 61/14
[52] U.S. Cl. ................................ 210/644; 210/652; 210/774
[58] Field of Search ............ 210/195.2, 634, 636, 210/644, 649–652, 767, 774, 804, 805, 806, 272.2

[56] References Cited

FOREIGN PATENT DOCUMENTS

| 0086028 | 5/1983 | European Pat. Off. . |
| 0152051 | 5/1985 | European Pat. Off. . |
| 2422569 | 11/1979 | France . |
| 2473313 | 7/1981 | France . |
| 60-197288 | 3/1984 | Japan . |
| 1000248 | 8/1965 | United Kingdom . |

Primary Examiner—Frank Sever
Attorney, Agent, or Firm—Oblon, Spivak, McClelland, Maier & Neustadt

[57] ABSTRACT

Sterilized and packaged mineral water comprises sterilized mineral water having a hardness of not less than 50 mg/l and a content of dissolved carbonic acid gas ranging from 9 to 30 mg/l (as calcium carbonate) and a number of bacteria of not more than $10^{-3}$/ml which is obtained by sterilizing pumped-up mineral water having a hardness of not less than 50 mg/l and a content of dissolved carbonic acid gas ranging from 10 to 31 mg/l by filtering through a filter having a pore size of not more than 0.22 $\mu$m. The packaged and sterilized mineral water can be effectively prepared by a method which comprises packaging pumped-up mineral water in a container without subjecting it to any heat-sterilization treatment wherein the mineral water is sterilized by passing through a filter having a pore size of not more than 0.22 $\mu$m, packaged in a sterilized container under an aseptic condition of not more than Class 100 and then the container is airtight-sealed. Thus, packaged and sterilized mineral water having excellent keeping quality can be obtained without subjecting pumped-up mineral water to any sterilization by heating and without using any antibacterial agent and it has a high hardness and a high carbon dioxide content as well as good taste peculiar to the original mineral water.

18 Claims, 2 Drawing Sheets

METHOD FOR PREPARING PACKAGED STERILIZED MINERAL WATER, METHOD FOR PRODUCING STERILIZED CONTAINER FOR PACKAGING THE SAME AND PACKAGED STERILIZED MINERAL WATER

BACKGROUND OF THE INVENTION

The present invention relates to a method for preparing sterilized mineral water without any heat-sterilization treatment, the mineral water being preferably free of an antibacterial agent and packaged in a container such as a bottle; a method for producing a container for packaging the mineral water; and the packaged mineral water per se.

There has been a demand for water having good taste and special water originated from various places have been packaged in containers and put on the market in great quantities. Since there is a possibility of propagation or proliferation of bacteria in pumped up, naturally occurring mineral water, there has, in general, been added chlorine to the pumped up mineral water to inhibit the subsequent propagation of bacteria (see Japanese Patent Unexamined Publication (hereinafter referred to as "J.P. Kokai") No. Sho 57-32779). However, it has been believed that if chlorine is added to mineral water, not only the natural taste of mineral water is deteriorated but also harmful substances such as trihalomethane are formed from the residual chlorine. On the other hand, there has been proposed a method in which mineral water is treated with chlorine and then with active carbon, but the natural taste pecuriar to each mineral water is impaired. Sterilization by heating is also an effective means, but the taste peculiar to each mineral water is likewise impaired.

Mineral water of high quality, in particular that having good taste has a high hardness and contains a large amount of carbon dioxide. However, if mineral water having a high hardness is subjected to the foregoing thermal sterilization treatment, components such as Ca and Mg which serve to increase the hardness of water in the form of bicarbonates are converted into carbonates, i.e., water-insoluble calcium or magnesium carbonates and thus precipitated out from the water and as a result, the hardness of water is greatly lowered.

Under such circumstances, there has been a need for the development of a method for preparing packaged mineral water in which pumped up mineral water is packaged in a container such as a bottle without addition of any antibacterial agent and without performing any thermal sterilization treatment and thereby the proliferation of bacteria in the mineral water is effectively prevented.

On the other hand, plastic bottles such as bottles of polyethylene terephthalate (PET) used for packaging mineral water have been generally sterilized by spraying an antibacterial agent such as hydrogen peroxide on the external and internal walls of the bottles. However, this method suffers from problems such that the taste of the contents thereof is impaired and that the residual antibacterial agent is bad for health of the persons who eat or drink the contents since a trace amount of the antibacterial agent remains unremoved on the walls of the bottle.

Thus, various attempts have been directed to the development of solutions of these problems. For instance, J.P. Kokai No. Sho 63-138931 discloses a method which comprises a sterilization-drying process in which an antibacterial agent is sprayed on a container and then hot air is blown onto the container to dry the same and a washing process for removing and washing away the antibacterial agent adhered to the external and internal walls of the container. In addition, J.P. Kokai No. Sho 60-99828 proposes a method comprising the step of spraying a solution of an antibacterial agent and then a washing solution on a container. However, in these methods, a large amount of washing solution is required for completely removing the antibacterial agent and the processes are very complicated.

SUMMARY OF THE INVENTION

A first object of the present invention is to provide a method for preparing packaged and sterilized mineral water having excellent keeping quality without subjecting pumped-up mineral water to any sterilization treatment by heating.

A second object of the present invention is to provide a method for preparing packaged and sterilized mineral water having excellent keeping quality without addition of any antibacterial agent to pumped-up mineral water.

A third object of the present invention is to provide a method for preparing sterilized mineral water which makes it possible to effectively prevent proliferation of bacteria in mineral water till the mineral water is packaged in a container such as a bottle after pumping up the mineral water without addition of any antibacterial agent.

A fourth object of the present invention is to provide a method for producing a sterilized container such as a bottle for packaging the sterilized mineral water which makes it possible to simply and efficiently sterilize the container without use of an antibacterial agent.

A fifth object of the present invention is to provide packaged and sterilized mineral water having a high hardness and a high carbon dioxide content as well as good taste and good keeping quality.

These and other objects of the present invention will be apparent from the following description and Examples.

According to a first aspect of the present invention, there is provided a method for preparing packaged and sterilized mineral water which comprises pumping up mineral water and then packaging the mineral water without subjecting it to any heat-sterilization treatment wherein the mineral water is sterilized by passing through a filter having a pore size of not more than 0.22 $\mu$m, packaged in a sterilized container under an aseptic condition of not more than Class 100 and then the container is airtight-sealed.

According to a second aspect of the present invention, there is provided a method for producing a sterilized plastic bottle for packaging sterlized mineral water which comprises the steps of standing a plastic bottle upside down, inserting a hot water-injecting nozzle into the bottle though an opening of the bottle, upwardly injecting hot water through the nozzle so that the injected hot water is discharged from the opening through the bottom and the side wall of the bottle to thus elevate the temperature of the inner wall of the bottle to a sterilization temperature.

According to a third aspect of the present invention, there is provided sterilized and packaged mineral water comprising sterilized mineral water having a hardness of not less than 50 mg/l and a content of dissolved carbonic acid gas ranging from 9 to 30 mg/l (as calcium carbonate) and a number of bacteria of not more than $10^{-3}$/ml which is obtained by sterilizing pumped-up mineral water having a hardness of not less than 50 mg/l and a content of dissolved carbonic acid gas ranging from 10 to 31 mg/l by filtering through a filter having a pore size of not more than 0.22 μm.

DESCRIPTION OF THE PREFERRED EMBODIMENTS

Figure 1:
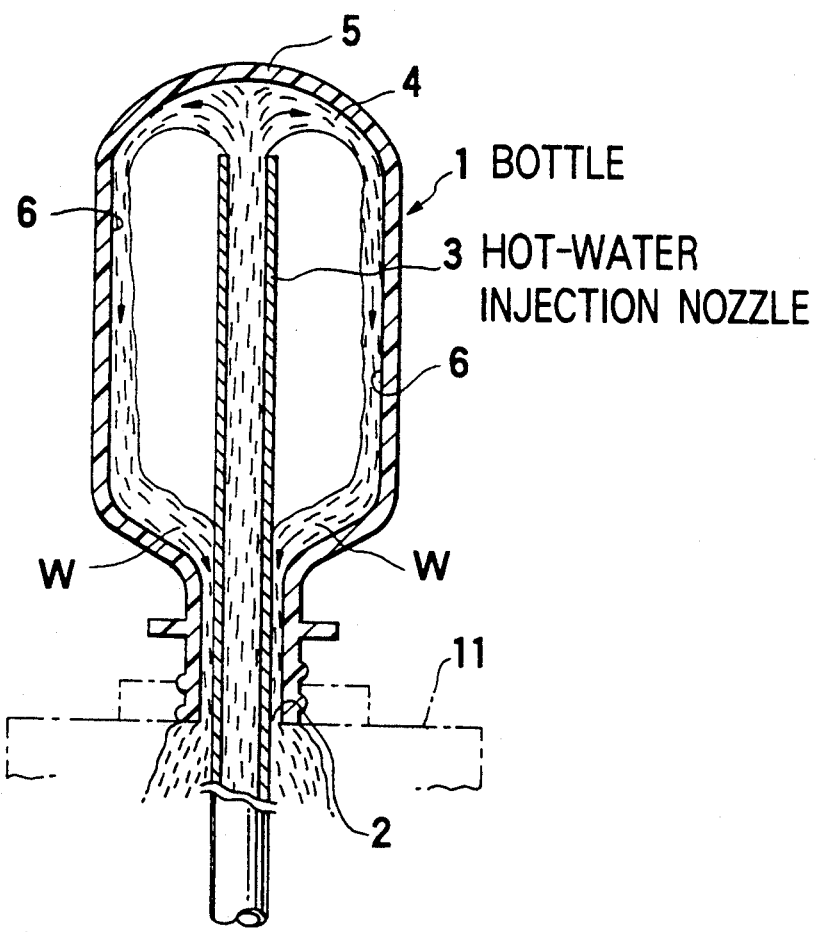
FIG. 1 is a schematic cross sectional view for explaining the sterilization treatment of the internal wall of a bottle according to the sterilization method of the present invention.

In the present invention, mineral water sterilized by passing through a filter having a pore size of not more than 0.22 μm is packaged in a sterilized container under an aseptic condition of not more than Class 100 and then airtight-sealed.

More specifically, pumped-up mineral water is desirably passed through a filter having a pore size of not more than 0.22 μm under the conditions for filtration of, for instance, an operating pressure ranging from about 1.0 to 2.0 kg/cm$^2$ and a flow rate of water ranging from about 5 to 20 l/min.m$^2$. According to this method, mineral water is not subjected to any heating process and, therefore, the taste of the mineral water is not deteriorated and hence the taste peculiar thereto can effectively be maintained. In other words, the filtration of mineral water through a filter having a pore size of not more than 0.22 μm permits effective removal of any bacteria present in the mineral water and thus the sterilization effect comparable to that achieved by high temperature heat-sterilization can be ensured. As the filer, there can be used a depth filter, membrane filter or the like in a suitable industrial manner such as cartridge type.

Incidentally, the pumped-up mineral water is in general stored in a tank after pumping up the same or transported by a tank truck to a packaging plant and then packaged in a container. Accordingly, bacteria possibly proliferate in the pumed-up mineral water during the storage and/or transportation. For this reason, pumped-up mineral water is preferably cooled at a temperature of not more than 12° C., preferably not more than 10° C. and in particular not more than 5° C. after the mineral water is pumped up till it is packaged in a container in order to prevent the proliferation or propagation of bacteria. In this connection, the lower limit of the cooling temperature is more than the freezing point of the mineral water. The temperature of mineral water pumped up from a groundwater zone is approximately constant in the order of 15° to 17° C. throughout the year, but a variety of bacteria are present in the pumped-up mineral water depending on the sources thereof or through the contamination with the bacterial present in the air during pumping up operations. For this reason, the foregoing treatment under the conditions specified above is needed.

Preferably, the foregoing cooling operation is compulsorily performed immediately after mineral water is pumped up from a ground-water zone.

The foregoing cooling treatment may be performed by the usual manner, but preferably carried out using a plate type refrigeration machine.

Morever, it is preferable that the pumped-up mineral water be filtered through a filter having a pore size of not more than 0.45 μm to compulsorily remove bacteria such as gram-negative bacteria possibly present in the water and water-insoluble matter. This method is preferable since harmful miocroorganisms can be removed prior to the subsequent sterilization treatment (i.e., the foregoing filtration treatment through a filter having a pore size of not more than 0.22 μm). This filtration treatment can be performed, for instance, in the same manner as described above in connection with the filtration by a filter having a pore size of not more than 0.22 μm. As such filters, there may be used, for instance, commercially available microfilters. Among them, preferred are those having a pore size of 0.45 μm because they make the filtration procedure easier. Either of the foregoing cooling treatment and the filtration procedure may be carried out in the method of this invention and if a combination of these two treatments is adopted, they may be carried out in any order.

The mineral water subjected to the foregoing treatments is preferably maintained at a low temperature of not more than 12° C. till it is subjected to a sterilization treatment. Therefore, when the mineral water is transported by a tank truck to a bottling plant, the mineral water is preferably maintained at a low temperature defined above during the transportation by a tank truck while if it is stored in a storage tank, the temperature of the storage tank is preferably maintained at such a low level defined above.

Then the mineral water which has thus been maintained at a low temperature is treated with a filtration film having a pore size of not more than 0.22 μm to completely remove various germs present therein prior to bottling.

In the present invention, the mineral water thus sterilized is packaged in a sterilized container in an aseptic atmosphere of not more than Class 100 and then airtight-sealed.

In the present invention, a known antibacterial agent such as a chlorine atom-containing bactericide may be added to the sterilized mineral water in the course of the sterilization treatment or after the treatment, but an excellent sterilization effect can be ensured even if any such bactericide is not added. Therefore, it is preferred that no bactericide be added to the mineral water.

Moreover, any mineral water obtained from various groundwater zones may be used in the present invention as starting materials, but it is desirable to use mineral water pumped up from a groundwater zone which has a hardness of not less than 50 mg/l, preferably 70 to 120 mg/l and a content of free carbonic acid in the form of dissolved carbon dioxide ranging from 10 to 31 mg/l (as calcium carbonate), preferably 12 to 17 mg/l. This is because, if such mineral water is used as starting water and the water is sterilized by the filtration as mentioned above, the resulting water has a hardness of not less than 50 mg/l, preferably 70 to 120 mg/l, a content of free carbonic acid of 9 to 30 mg/l, preferably 11 to 16 mg/l and a number of bacteria of not more than $10^{-3}$/ml, so that the sterilized mineral water having high quality, in view of its taste can easily be obtained. Therefore, if the hardness and the content of carbon dioxide of starting water are less than the lower limits thereof, these properties are preferably adjusted so as to fall within the ranges defined above respectively. The term "hardness" herein means the overall hardness which is the sum of the temporary hardness and the permanent hardness.

In the present invention, examples of the containers are plastic bottles, glass bottles and cans which are sterilized in the usual manner, but they are preferably sterilized by heat-treating with moist heat under the following conditions. This is because the resulting mineral water is not contaminated with any antibacterial agent since the sterilization treatment does not requires the use of an antibacterial agent.

For instance, if a bottle is used as a container and it is sealed with a cap, the bottle and the cap are wet-sterilized such that the inner walls thereof are maintained under conditions equivalent to exposure to a temperature of 70° C. for 10 seconds or more severe conditions, provided that the temperature is not higher than the heat-resisting temperature of the bottle and the cap. In this respect, the conditions equivalent to exposure to a temperature of 70° C. for 10 seconds can be obtained from the following formula:

$$\log y = 1 - (x - 70)/10$$

(wherein x represents the temperature (°C.) of the inner wall of a bottle or cap and y means a retention time (seconds)).

In general, the heat-resisting temperature of plastic bottles and caps is low. Accordingly, they can be effectively sterilized under these conditions without causing any deformation. In this respect, if the sterilization is performed under the conditions corresponding to heating at less than 70° C. for less than 10 seconds, a satisfactory sterilization effect cannot often be achieved. A better sterilization effect can be ensured if a bottle and a cap are treated under the conditions such that the inner wall of the bottle or cap is maintained at 75° C. or higher or under the conditions corresponding to heating at a temperature of not less than 75° C. for not less than 10 seconds.

Examples of bottles to be sterilized according to the method of this invention include plastic bottles oriented by blow molding such as those of polyethylene, polypropylene and polyethylene terephthalate (PET). Particularly preferred are those made of PET. In addition, examples of caps include those formed from plastic materials listed above and those made from metals such as aluminum. Among these, preferred are those formed from aluminum.

Upon subjecting the foregoing bottle to wet-sterilization, preferably used is a method which comprises the steps of standing a plastic bottle upside down, inserting a hot-water injection nozzle into the bottle through an opening of the bottle, upwardly injecting hot water through the nozzle so that the injected hot water is discharged from the opening through the bottom and the side wall of the bottle to thus elevate the temperature of the inner wall of the bottle to a sterilization temperature. For instance, as shown in FIG. 1, an opening 2 of a bottle 1 is directed towards downward direction, preferably just downward direction and a hot-water injection nozzle 3 is inserted into the bottle 1 through the opening 2. Then hot water is upwardly injected through the nozzle 3 so that the injected hot water 4 is discharged from the opening 2 through a bottom wall 5 and a side wall 6 of the bottle to thus elevate the temperature of the inner wall of the bottle to a sterilization temperature. At this stage, the hot-water injection nozzle 3 is inserted into the bottle 1 so that the tip of the nozzle 3 does not come in contact with the hot water W which flows down through the bottom and the side wall of the bottle 1. More specifically, according to this method, the hot water injected through the nozzle 3 does not come in contact with the hot water W which comes in contact with the inner wall of the bottle and flows down towards the opening of the bottle and, therefore, the tip of the hot-water injection nozzle is not contaminated and the hot water carrying a desired quantity of heat can be effectively supplied to the wall of the bottle. Thus, the method makes it possible to steadily elevate the temperature of the inner wall of the bottle up to the sterilization temperature.

Moreover, if a cylindrical hot-water injection nozzle 3 is employed, the hot water can effectively flow down through the bottom and the side wall of the bottle 1.

To achieve the sterilization conditions defined above, a cylindrical nozzle 1 having an inner diameter of 8 to 10 mm, preferably 9 to 10 mm is used as the hot-water injection nozzle 3 and hot water having a temperature of the bottle 1 is desirably injected into the bottle. In this case, the overall amount of the hot water to be injected having a temperature ranging from 75° to 90° C. ranges from 0.2 to 2 times, preferably 0.5 to 1 time that of the inner volume of the bottle to be sterilized and the hot water is preferably injected through the nozzle 3 at a rate ranging from 10 to 30 l/min. Thus, the inner wall of the bottle can be effectively and uniformly sterilized.

On the other hand, the moist heat-sterilization of caps can be performed by, for instance, injecting hot water into the caps as in the sterilization of bottles, passing the caps through hot water or coming the caps in contact with steam or hot air. For instance, a metal cap is preferably sterilized by coming the inner wall thereof in contact with steam and, in this case, the metal cap may also be sterilized by passing through a steam tunnel maintained at a temperature ranging from 95° to 100° C. for a retention time ranging from about 3 to 15 seconds.

Satisfactory sterilization and simultaneous washing of these bottles and caps can be performed by carrying out the sterilization treatment of them according to the foregoing methods, but the temperature of the inner walls of the bottle and cap is raised to a desired sterilization temperature by the action of hot water while heating the external walls thereof to thus maintain the temperature of them at the sterilization temperature for a desired time period in order to further improve the sterilization efficiency. Specifically, the external walls of the bottle and cap are preferably heated by coming in contact with hot water, steam or hot air. In particular, when the external wall is heated with hot water, it is effective that the hot water is sprayed on the bottle from the upper side and/or from the right and left side thereof. This method is more preferable than those in which steam or hot air is employed, in that the temperature control is relatively easy and that the deformation of the bottle can effectively be prevented. Moreover, the method for spraying hot water from the upper side of the bottle is preferred because the heat of the hot water is uniformly transferred to the external wall of the bottle. The foregoing can likewise be applied to the treatment of caps.

If the foregoing external sterilization treatment is carried out while the sterilization temperature attained by the internal sterilization treatment has still been maintained, the bottle is further maintained at the sterilization temperature, for instance, ranging from 70° to 90° C. for an additional predetermined time.

In the foregoing method, hot water having a temperature ranging from 70° to 95° C., preferably 75° to 95° C. is sprayed on the external wall of the bottle for 1 to 20 seconds, preferably 3 to 15 seconds in an amount ranging from 10 to 1,000 l per bottle. When steam is used instead of hot water, steam having a pressure ranging from 0.2 to 0.5 kg/cm² (gauge pressure) is preferably sprayed onto the external wall of the bottle for 3 to 15 seconds, while if hot air is employed, hot air having a temperature ranging from 80° to 100° C. is preferably blown on the external wall of the bottle for 3 to 15 seconds.

A combination of internal and external sterilization treatments is adopted in the foregoing method and, therefore, quite efficient and complete sterilization can be accomplished.

Figure 2:
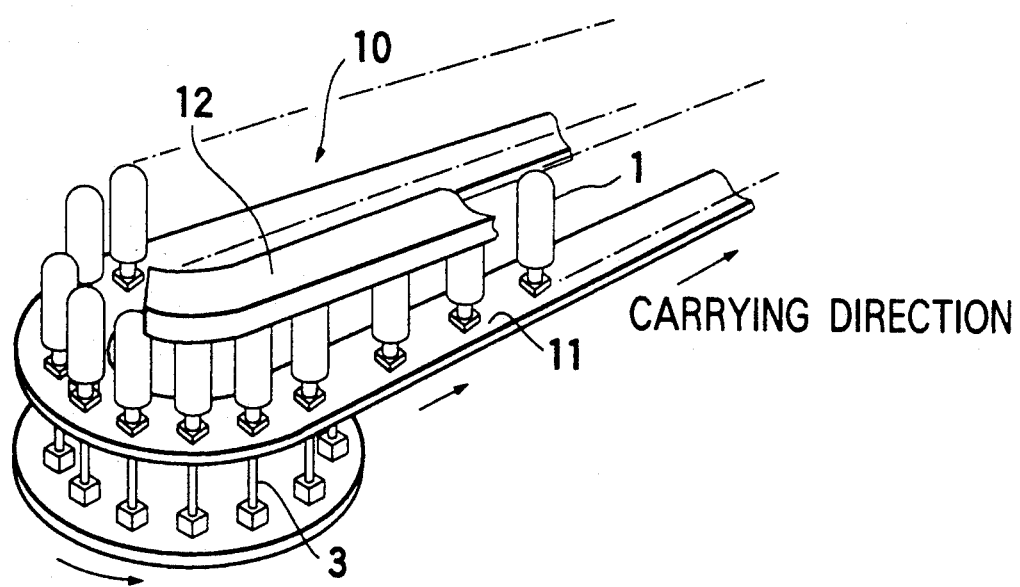
FIG. 2 is a schematic perspective view of an apparatus for practicing the sterilization method of the present invention.

Industrially, the foregoing sterilization treatment of bottles can be performed continuously with the aid of, for instance, an apparatus 10 as shown in FIG. 2. In FIG. 2, the numerical value 11 represents a conveying device and a bottle 1 is transported towards the carrying direction shown in the figure while hot water is injected in the bottle through a hot-water injection nozzle 3 and sprayed onto the bottle from the upper side thereof through a hot-water shower portion 12.

Most preferably, the foregoing sterilized mineral water is packaged in a bottle which has been sterilized according to the foregoing method and airtightly sealed with a cap which has been sterilized in the same manner.

As has been discussed above in detail, according to the present invention, there can be provided a method for preparing packaged and sterilized mineral water excellent in keeping quality, in which pumped-up mineral water as a starting material is not sterilized by heating and any antibacterial agent is not used at all. Thus, the method of the present invention can provide excellent mineral water whose natural taste can be well-maintained.

The present invention will hereunder be explained in more detail with reference to the following non-limitative working Examples.

EXAMPLE 1

(i) Sterilization Treatment of Bottle

A PET bottle having an inner volume of 1,500 cc, a shape similar to that shown in FIG. 1 and an opening part having an inner diameter of 21 mm was subjected to internal and external washing treatments under the conditions detailed below with the aid of an apparatus as shown in FIG. 2.

Internal Washing Treatment

The PET bottle was fixed to a conveying device while standing the bottle upside down, a hot-water injection nozzle was inserted into the bottle through the opening at the region of this side of FIG. 2 in which the bottle was conveyed on a circle and the hot water was upwardly injected therein so that the hot water was discharged from the opening through the bottom and side wall of the bottle. The hot-water injection treatment was performed by injecting 1,200 cc of hot water having a temperature of 85° C. through the nozzle at a rate of 13,000 cc/min. The hot-water injection nozzle used herein was a cylindrical nozzle having an inner diameter of 9 mm. The foregoing treatment was performed so that the inner wall of the bottle was maintained at 80° C. for 3 seconds.

External Washing Treatment

The PET bottle was transferred from the foregoing position to a position for spraying hot water, 10,000 cc of hot water was sprayed for 5 seconds onto the bottle through a shower board disposed above the bottle to perform external washing to thus obtain a bottle which was sterilized completely from the viewpoint of microorganisms. The external washing was started at the second half of the internal washing.

Sterilization Treatment of Cap

An aluminum cap having an inner diameter of 28 mm φ and a height of 18 mm was supplied to a sterilizing chamber in its standing state and the whole surface of the cap was brought into contact with steam of 100° C. for 5 seconds to perform sterilization of the cap. The inner wall of the cap was maintained at 80° C. for 3 seconds by the foregoing treatment.

Sterilization Treatment of Mineral Water

Mineral water pumped up from a well (the temperature thereof immediately after pumping up was 17° C.) was filtered through a filter cloth to remove foreign substance. The mineral water was cooled down to 5° C. immediately after pumping up the same using a plate type refrigeration machine. The cooled mineral water was subjected to precision filtration by passing through a filter having a pore size of 0.45 μm. The mineral water thus treated was transported to a bottling plant and stored in a storage tank in the bottling plant. The mineral water was maintained at a temperature of not more than 10° C. from its pumping up till it was introduced into the storage tank and during storage in the tank.

The mineral water which had been stored for about 8 hours in the storage tank was treated with active carbon, subjected to precision filtration by passing through a filter having a pore size of 0.22 μm, packaged in the PET bottle sterilized above under the aseptic condition of not more than class 100 and sealed with the cap likewise sterilized above to give packaged sterilized mineral water.

The resulting mineral water could be stored for about 18 months at ordinary temperature without any trouble and, for instance, it maintained the taste peculiar thereto even after 12 months storage at ordinary temperature.

EXAMPLE 2

Mineral water pumped up from a well (the temperature thereof immediately after pumping up was 17° C.) was filtered through a filter cloth to remove foreign substance. The mineral water was cooled down to 5° C. with the aid of a plate type refrigeration machine immediately after pumping up the same. The cooled mineral water was stored in a storage tank. The mineral water was maintained at a temperature of not more than 100° C. from its pumping up till it was introduced into the storage tank and during storage in the tank.

The mineral water which had been stored for about 4 hours in the storage tank was treated with active carbon; filtered to sterilize the mineral water in the same manner used in Example 1, packaged in a synthetic resin-bottle likewise sterilized in the same manner used in Example 1 under the aseptic condition of not more than class 100 and sealed with a cap likewise sterilized in the same manner used in Example 1 to give packaged and sterilized mineral water.

The resulting mineral water could be stored for about 18 months at ordinary temperature without any trouble and, for instance, it maintained the taste peculiar thereto even after 12 months storage at ordinary temperature.

EXAMPLE 3

Mineral water pumped up from a well (hardness 80 mg/l; content of free carbonic acid (dissolved carbonic acid gas) 13 mg/l (as calcium carbonate); number of bacteria 30/ml; the temperature thereof immediately after pumping up 17° C.) was filtered through a filter cloth to remove foreign substance. The mineral water was cooled down to 5° C. immediately after its pumping up using a plate type refrigeration machine. The cooled mineral water was subjected to precision filtration by passing through a filter having a pore size of 0.45 $\mu$m with the aid of a pressure filtration device.

The mineral water thus treated was transported to a bottling plant and stored in a storage tank in the bottling plant. The mineral water was maintained at a temperature of not more than 10° C. from its pumping up till it was introduced into the storage tank and during storage in the tank.

The mineral water which had been stored for about 12 hours in the storage tank was treated with active carbon, subjected to precision filtration by passing through a filter having a pore size of 0.22 $\mu$m using a pressure filtration device to give sterilized mineral water. The foregoing filtration procedure was carried out at 15° C. The resulting mineral water had a hardness of 80 mg/l, a content of free carbonic acid of 12 mg/l and number of bacteria of not more than $10^{-5}$/ml.

The mineral water thus obtained was packaged in a sterilized bottle of a synthetic resin under the aseptic condition of not more than class 100 and sealed with a sterilized cap to give packaged sterilized mineral water. The bottle was sterilized by maintaining at 75° C. for 10 seconds using hot water and the cap was sterilized by maintaining at 100° C. for 5 seconds using steam.

The resulting mineral water had a viable count (number of bacteria capable of proliferating in the mineral water) of $10^{-5}$/ml and could be stored for about 18 months at ordinary temperature without any trouble and, for instance, it maintained the taste peculiar thereto even after 12 months storage at ordinary temperature.

EXAMPLE 4

Mineral water pumped up from a well (hardness 80 mg/l; content of free carbonic acid 13 mg/l; number of bacteria 30/ml; the temperature thereof immediately after pumping up 17° C.) was filtered through a filter cloth to remove foreign substance. The mineral water was then treated with activated carbons, subjected to precision filtration by passing through a filter having a pore size of 0.22 $\mu$m with the aid of a pressure filtration device to obtain sterilized mineral water. The filtration was carried out at a temperature of 15° C. The thus-obtained mineral water had a hardness of 80 mg/l, content of free carbonic acid of 12 mg/l and number of bacteria of not ore than $10^{-5}$/ml.

The mineral water thus obtained was packaged in a sterilized bottle of a synthetic resin and sealed with a sterilized cap under the same conditions used in Example 1 to give packaged sterilized mineral water.

The resulting mineral water had a viable count (number of bacteria capable of proliferating in the mineral water) of $10^{-5}$/ml and could be stored for about 18 months at ordinary temperature without any trouble and, for instance, it maintained the taste peculiar thereto even after 12 months storage at ordinary temperature.

We claim:

1. A method for preparing packaged and sterilized mineral water which comprises packaging pumped-up mineral water in a container without subjecting it to any heat-sterilization treatment, the method comprising the steps of:
    (a) pumping up mineral water from a groundwater zone,
    (b) cooling the pumped-up mineral water to a temperature of not more than 12° C.,
    (c) filtering the mineral water by passing through a filter having a pore size of 0.45 $\mu$m.,
    (d) sterilizing the mineral water by passing through a filter having a pore size of not more than 0.22 $\mu$m, and
    (e) packaging the resulting mineral water in a sterilized container under an aseptic condition of not more than class 100 and then airtight-sealing the container.

2. The method of claim 1 wherein the pumped-up mineral water is cooled to a temperature of not more than 10° C.

3. The method of claim 2 wherein the pumped-up mineral water is cooled to a temperature of not more than 5° C.

4. The method of claim 1 wherein the container comprises a plastic bottle and a cap for sealing the bottle.

5. The method of claim 4 wherein the plastic bottle is made of polyethylene terephthalate.

6. A method for producing a sterilized container as claimed in claim 4 comprising subjecting the container to wet-sterilization such that the inner wall of the container is maintained under conditions equivalent to exposure to a temperature of 75° C. for 10 seconds or more severe conditions, provided that the temperature is not higher than the heat resisting temperature of the container.

7. A method for producing a sterilized container as claimed in claim 5 comprising the steps of standing the plastic bottle upside down, inserting a hot-water injection nozzle into the bottle through an opening of the bottle such that its tip does not come in contact with the hot water flowing down through the bottom and side wall of the bottle, upwardly injecting hot water through the nozzle so that the injected hot water is discharged from the opening through the bottom and the side wall of the bottle to this elevate the temperature of the inner wall of the bottle to such a sterilization temperature that the inner wall of the container is maintained under conditions equivalent to exposure to a temperature of 70° C. for 10 seconds or more severe conditions, provided that the temperature is not higher than the heat resisting temperature of the container.

8. The method of claim 7 wherein a nozzle having an inner diameter ranging from 8 to 10 mm is used as the hot-water injection nozzle and hot water having a temperature of not less than 70° C. and not more than the heat resisting temperature of the bottle is injected through the nozzle.

9. The method of claim 7 wherein hot water having a temperature ranging from 75° to 90° C. is injected through the nozzle in an amount of 0.2 to 2 times the volume of the bottle per bottle.

10. The method of claim 7 wherein the temperature of the inner wall of the bottle is raised to the sterilization temperature while the external wall of the bottle is heated to maintain the bottle at the sterilization temperature for a desired time period.

11. The method of claim 10 wherein the heating of the external wall of the bottle is performed by bringing the wall in contact with hot water, steam or hot air.

12. The method of claim 10 wherein the heating of the external wall of the bottle is performed by showering hot water having a temperature of not less than 70° C. and not more than the heat resisting temperature of the bottle.

13. The method of claim 1 wherein the sterilization treatment by filtration is carried out using a pressure filtration device.

14. The method of claim 13 wherein the sterilization treatment by filtration is carried out an operational pressure ranging from 1.0 to 2.0 kg/cm$^2$ and a flow rate of water ranging from 5 to 20 l/min.m$^2$.

15. Sterilized and packaged mineral water prepared by the method of claim 1 comprising sterilized material water having a hardness of not less than 50 mg/l and a content of dissolved carbonic acid gas (as calcium carbonate) ranging from 9 to 30 mg/l and a number of bacteria of not more than $10^{-3}$/ml which is obtained by sterilizing pumped-up mineral water having a hardness of not less than 50 mg/l and a content of dissolved carbonic acid gas ranging from 10 to 31 mg/l by filtering through a filter having a pore size of not more than 0.22 μm.

16. The method of claim 1 wherein the temperature of the mineral water is maintained at not more than 12° C. after the mineral water is pumped up until it is sterilized.

17. The method of claim 1 wherein the pumped-up mineral water is cooled down to a temperature of not ore than 10° C.

18. The method of claim 1 wherein the pumped-up mineral water is cooled down to a temperature of not more than 5° C.

* * * * *